(12) United States Patent
Rothman

(10) Patent No.: US 10,888,552 B2
(45) Date of Patent: Jan. 12, 2021

(54) TREATMENT OF DISORDERS OF SEXUAL AROUSAL WITH LOCAL APPLICATION OF AGENTS THAT INCREASE MEMBRANE EXCITABILITY

(71) Applicant: Steven Rothman, Clayton, MO (US)

(72) Inventor: Steven Rothman, Clayton, MO (US)

(73) Assignee: Steven Rothman, Clayton, MO (US)

( * ) Notice: Subject to any disclaimer, the term of this patent is extended or adjusted under 35 U.S.C. 154(b) by 0 days.

(21) Appl. No.: 16/313,534

(22) PCT Filed: Jul. 21, 2017

(86) PCT No.: PCT/US2017/043222
§ 371 (c)(1),
(2) Date: Dec. 27, 2018

(87) PCT Pub. No.: WO2018/031216
PCT Pub. Date: Feb. 15, 2018

(65) Prior Publication Data
US 2019/0192493 A1    Jun. 27, 2019

Related U.S. Application Data

(60) Provisional application No. 62/374,303, filed on Aug. 12, 2016.

(51) Int. Cl.
*A61K 31/4409*    (2006.01)
*A61K 31/4422*    (2006.01)
*A61K 31/14*    (2006.01)
*A61K 31/4748*    (2006.01)
*A61K 33/00*    (2006.01)
*A61P 15/00*    (2006.01)
*A61P 15/12*    (2006.01)

(52) U.S. Cl.
CPC .......... *A61K 31/4409* (2013.01); *A61K 31/14* (2013.01); *A61K 31/4422* (2013.01); *A61K 31/4748* (2013.01); *A61K 33/00* (2013.01); *A61P 15/00* (2018.01); *A61P 15/12* (2018.01)

(58) Field of Classification Search
None
See application file for complete search history.

(56) References Cited

U.S. PATENT DOCUMENTS

| | | | |
|---|---|---|---|
| 3,038,858 A | 6/1962 | Verley et al. | |
| 4,521,401 A | 6/1985 | Dunn | |
| 5,624,675 A * | 4/1997 | Kelly | A61K 31/315 424/405 |
| 8,007,826 B2 | 8/2011 | Blight et al. | |
| 2005/0065158 A1 | 3/2005 | Naylor et al. | |
| 2005/0276851 A1 * | 12/2005 | Cunningham | A61P 43/00 424/468 |
| 2005/0288270 A1 * | 12/2005 | Allerton | C07D 401/04 514/210.2 |
| 2009/0215810 A1 * | 8/2009 | Singh | A61K 31/135 514/289 |
| 2012/0009283 A1 | 1/2012 | Bombardelli | |
| 2015/0157615 A1 | 6/2015 | Segalla | |

FOREIGN PATENT DOCUMENTS

EP    1980252 A2    10/2008
WO    199709046 A1    3/1997

OTHER PUBLICATIONS

Arnold et al., Ion Channel Modulation as a Therapeutic Approach in Multiple Sclerosis; Current Medicinal Chemistry, 2015, vol. 22, pp. 4366-4378.
Bever et al., Sustained-release fampridine for multiple sclerosis; Drug Evaluation; 12-pages.
Bostock et al., The Effects of 4-Aminopyridine and Tetraethylammonium Ions on Normal and Demyelinated Mammalian Nerve Fibres; J. Physiol., 1981, vol. 313, pp. 301-315.
Bowe et al, Differences between mammalian ventral and dorsal spinal roots in response to blockade of potassium channels during maturation; Proc. R. Soc. Lond. B, 1985, vol. 224, pp. 355-366.
Bowe et al., Physiological Effects of 4-Aminopyridine on Demyelinated Mammalian Motor and Sensory Fibers; 5-pages.
Cardenas et al., Phae 2 trial of sustained-release fampridine in chronic spinal cord injury; Spinal Cord, 2007, vol. 45, pp. 158-168.
Targ et al., 4-Aminopyridine leads to restoration of conduction in demyelinated rat sciatic nerve; Brain Research, 1985, vol. 328, pp. 358-361.
Targ et al., Action Potential Characteristics of Demyelinated Rat Sciatic Nerve following Application of 4-Aminopyridine; Brain Research, 2986, vol. 363, pp. 1-9.
Yang et al., Focal Cooling Rapidly Terminates Experimental Neocortical Seizures; Ann Neurol, 2001, vol. 49, pp. 721-726.

\* cited by examiner

*Primary Examiner* — Sin J Lee
(74) *Attorney, Agent, or Firm* — Stinson LLP

(57) ABSTRACT

Compositions and methods for stimulating erogenous zones of female and male subjects are disclosed. More particularly, the present disclosure relates to compositions for topical application to the female and male genitalia that increase cell membrane excitability and to methods of using the compositions for treating sexual dysfunction and enhancing sexual arousal and facilitating orgasm.

3 Claims, No Drawings

TREATMENT OF DISORDERS OF SEXUAL AROUSAL WITH LOCAL APPLICATION OF AGENTS THAT INCREASE MEMBRANE EXCITABILITY

CROSS REFERENCE TO RELATED APPLICATIONS

This application is a U.S. National Phase Application of PCT/US2017/043222 (published as WO 2018/031216), filed on Jul. 21, 2017, which claims priority to U.S. Provisional Patent Application Ser. No. 62/374,303, filed on Aug. 12, 2016, the disclosures of which are hereby incorporated by reference in their entireties.

BACKGROUND OF THE DISCLOSURE

The present disclosure relates generally to compositions and methods for enhancing sexual arousal and treating female orgasmic disorder. More particularly, the present disclosure relates to compositions for topical application to the female and male genitalia that increase cell membrane excitability and to methods of using the compositions for enhancing sexual arousal and facilitating orgasm. Also disclosed are methods for treating female orgasmic disorder.

Sexual dysfunction is extremely common in both sexes, possibly affecting up to 40% of women (Houman et al., Current Urology Reports 2016, 17:28). There are a variety of therapies for males with sexual dysfunction, mostly focused on therapy of erectile dysfunction with drugs that inhibit phosphodiesterase 5, elevating levels of cyclic guanine monophosphate and promoting smooth muscle relaxation. This strategy has been largely ineffective for women, even when it results in clitoral engorgement. A recently released mixed serotonin receptor agonist/antagonist which was designed to treat female sexual dysfunction has also not proved spectacularly effective (Jaspers et al., JAMA Internal Medicine 2016; 176:453-62).

There is unlikely to be a single, simple explanation, and then resulting therapy for female sexual dysfunction. However, one strategy that has largely been ignored in attempting to treat female sexual dysfunction is locally acting drugs that could enhance vaginal and clitoral sensation. There are a variety of drugs which are known to increase the excitability of neurons and their axons. The best characterized of these is 4-aminopyridine (4-AP).

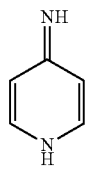

4-AP

Over 30 years ago, physiologists demonstrated that it blocked potassium channels in neuronal cell bodies and axons (Bostock et al., The Journal of Physiology 1981; 313:301-15; Sherratt et al., Nature 1980; 283:570-2). Other investigators have specifically shown that 4-AP affects the potassium channels of dorsal root ganglion neurons, which mediate cutaneous sensitivity (Bowe et al., Annals of Neurology 1987; 22:264-8; Bowe et al., Proceedings of the Royal Society of London Series B, Biological Sciences 1985; 224:355-66; Targ and Kocsis, Brain Research 1985; 328:358-61; Targ and Kocsis, Brain Research 1986; 363:1-9). There is even evidence that 4-AP can increase the firing rate of nerve fibers under some conditions (Bowe et al., Annals of Neurology 1987; 22:264-8; Targ and Kocsis, Brain Research 1985; 328:358-61). In the central nervous system, this effect is very easy to identify, and 4-AP has been used experimentally to induce animal seizures (Yang and Rothman, Annals of Neurology 2001; 49:721-6).

Since the studies cited above were carried out, other clinical investigators showed that 4-AP could improve neurological function in patients with multiple sclerosis and damaged spinal cord and cerebral myelinated axons (Bever et al., Neurology 1994; 44:1054-9; Potter et al., Spinal Cord 1998; 36:147-55). While there was concern that 4-AP might produce unacceptable side effects if used in humans, it has recently been formulated in an oral extended release preparation for the treatment of spasticity and other neurological problems in patients with multiple sclerosis and other types of central nervous system injury (Arnold et al., Current Medicinal Chemistry 2015; 22:4366-78; Cardenas et al., Spinal Cord 2007; 45:158-68). This extended release formulation of 4-AP has been described in several US patents assigned to Acorda Therapeutics (e.g. U.S. Pat. No. 8,007, 826) and the formulation has been approved by the FDA for clinical use as dalfampridine (AMPYRA®). Interestingly, the neurological side effects include seizures, dizziness, and skin burning and tingling, all indicative of neuronal overactivity.

While there are a variety of therapies for treating sexual dysfunction and enhancing sexual arousal, the current strategies have been largely ineffective, particularly for women. Accordingly, there exists a need for compositions and methods of using the compositions for treating sexual dysfunction and enhancing sexual arousal.

BRIEF DESCRIPTION OF THE DISCLOSURE

The present disclosure is generally directed to compositions and methods of using the compositions for enhancing sexual arousal. More particularly, the present disclosure relates to compositions for topical application to the female and male genitalia that increase cell membrane excitability and to methods of applying the compositions for enhancing sexual arousal and facilitating orgasm.

In one aspect, the present disclosure is directed to a composition comprising a potassium channel inhibitor and a lubricant.

In one aspect, the present disclosure is directed to a composition comprising a tetraethylammonium chloride and a lubricant.

In one aspect, the present disclosure is directed to a composition comprising potassium and a lubricant.

In one aspect, the present disclosure is directed to a composition comprising a sodium channel activator and a lubricant.

In one aspect, the present disclosure is directed to a composition comprising a divalent cation chelator and a lubricant.

In one aspect, the present disclosure is directed to a method for treating sexual dysfunction in a subject in need thereof, the method comprising: topically applying to the subject's genitalia a composition selected from the group consisting of a composition comprising a potassium channel blocker and a lubricant; a composition comprising tetraethylammonium chloride and a lubricant; a composition comprising potassium and a lubricant; and a composition comprising a sodium channel activator and a lubricant.

In one aspect, the present disclosure is directed to a method for stimulating erogenous zones of a subject in need thereof, the method comprising: topically applying to the subject's genitalia a composition selected from the group consisting of a composition comprising a potassium channel blocker and a lubricant; a composition comprising tetraethylammonium chloride and a lubricant; a composition comprising potassium and a lubricant; and a composition comprising a sodium channel activator and a lubricant.

In one aspect, the present disclosure is directed to a method for treating female orgasmic disorder in a subject in need thereof, the method comprising: topically applying to the subject's genitalia a composition selected from the group consisting of a composition comprising a potassium channel blocker and a lubricant; a composition comprising tetraethylammonium chloride and a lubricant; a composition comprising potassium and a lubricant; and a composition comprising a sodium channel activator and a lubricant.

In accordance with the present disclosure, compositions and methods have been discovered that allow for enhancing sexual arousal and treating female orgasmic disorder. More particularly, the present disclosure relates to compositions for topical application to the female and male genitalia that increase cell membrane excitability and to methods of applying the compositions for enhancing sexual arousal and facilitating orgasm.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein and in the appended claims, the singular forms "a", "an", and "the" include plural reference unless the context clearly dictates otherwise.

As used herein "topical application" refers to direct administration by a non-systemic route at or in the vicinity of the site of application.

The terms "pharmaceutically acceptable salts, esters, amides, and prodrugs" as used herein refer to those carboxylate salts, amino acid addition salts, esters, amides, and prodrugs of the compounds of the present disclosure that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds of the invention.

Compositions

In one aspect, the present disclosure is directed to a composition including a potassium channel blocker and a lubricant.

Suitable lubricants include, for example, water-based lubricants, oil-based lubricants, and silicone-based lubricants. Particularly suitable lubricants include, for example, glycerin, hydroxyethyl cellulose, xylitol, carrageenan, and combinations thereof.

In one embodiment, the potassium channel blocker is a pyridine potassium channel blocker. Suitable pyridine potassium channel blockers include aminopyridines. Particularly suitable aminopyridines include, for example, 4-aminopyridine; 2-aminopyridine; 3-aminopyridine; 2,3-diaminopyridine; 3,4-diaminopyridine and combinations thereof.

In another embodiment, the potassium channel blocker can be quinidine ((S)-(6-Methoxyquinolin-4-yl)[(1S,2R,4S,5R)-5-vinylquinuclidin-2-yl]methanol), ibutilide (N-(4-{4-[ethyl(heptyl)amino]-1-hydroxybutyl}phenyl)methanesulfonamide), propafenone (1-{2-[2-Hydroxy-3-(propylamino)propoxy]phenyl}-3-phenylpropan-1-one) (1-30 microM), amiodarone ((2-{4-[(2-butyl-1-benzofuran-3-yl)carbonyl]-2,6-diiodophenoxy}ethyl)diethylamine), vernakalant ((3R)-1-{(1R,2R)-2-[2-(3,4-dimethoxyphenyl)ethoxy]cyclohexyl}pyrrolidin-3-ol), dofetilide (N-[4-(2-{[2-(4-methane sulfonamidophenoxy)ethyl](methyl)amino}ethyl)phenyl]methanesulfonamide), dronedarone (N-(2-Butyl-3-(p-(3-(dibutylamino)propoxy)benzoyl)-5-benzofuranyl)methanesulfonamide), and combinations thereof.

The amount of the potassium channel blocker in the composition varies depending on the desired dose for efficient drug delivery, the molecular weight, and the activity of the compound. The actual amount of the potassium channel blocker can depend on the patient's age, weight, sex, medical condition, disease or any other medical criteria. Further, the amount of the potassium channel blocker, salt, solvated, or prodrug thereof included in the composition of the present disclosure can vary, depending upon a variety of additional factors, including, for example, the specific potassium channel blocker used, the desired dosage level, the type and amount of lubricant used, and the presence, types and amounts of additional materials included in the composition. The actual amount of the potassium channel blocker can be determined according to intended use by techniques known in the art. In one embodiment, the potassium channel blocker is present in the composition in amounts ranging from about 1 µM to about 10 mM, including ranges of from about 1 µM to about 2 mM, and including ranges of from about 10 µM to about 10 mM. For example, when the potassium channel blocker is an aminopyridine, the aminopyridine is present in the composition in an amount ranging from about 0.1 mM to about 10 mM. Suitably, the aminopyridine is present in the composition in an amount ranging from about 0.1 mM to about 2 mM. In another exemplary embodiment, the potassium channel blocker is quinidine ((S)-(6-Methoxyquinolin-4-yl)[(1S,2R,4S,5R)-5-vinylquinuclidin-2-yl]methanol) and is present in the composition in an amount ranging from about 1 µM to about 30 µM. In another exemplary embodiment, the potassium channel blocker is ibutilide (N-(4-{4-[ethyl(heptyl)amino]-1-hydroxybutyl}phenyl)methanesulfonamide) and is present in the composition in an amount ranging from about 1 nM to about 30 nM. In another exemplary embodiment, the potassium channel blocker is propafenone (1-{2-[2-Hydroxy-3-(propylamino)propoxy]phenyl}-3-phenylpropan-1-one) and is present in the composition in an amount ranging from about 1 µM to about 30 µM. In another exemplary embodiment, the potassium channel blocker is amiodarone ((2-{4-[(2-butyl-1-benzofuran-3-yl)carbonyl]-2,6-diiodophenoxy}ethyl)diethylamine) and is present in the composition in an amount ranging from about 1 µM to about 30 µM. In another exemplary embodiment, the potassium channel blocker is vernakalant ((3R)-1-{(1R,2R)-2-[2-(3,4-dimethoxyphenyl) ethoxy]cyclohexyl}pyrrolidin-3-ol) and is present in the composition in an amount ranging from about 1 µM to about 30 µM. In another exemplary embodiment, the potassium channel blocker is dofetilide (N-[4-(2-{[2-(4-methane sulfonamidophenoxy)ethyl](methyl)amino}ethyl)phenyl]methanesulfonamide) and is present in the composition in an amount ranging from about 1 nM to about 30 nM. In another exemplary embodiment, the potassium channel blocker is dronedarone (N-(2-Butyl-3-(p-(3-(dibutylamino)propoxy)benzoyl)-5-benzofuranyl)methanesulfonamide) and is present in the composition in an amount ranging from about 1 µM to about 10 µM. The composition can be administered one or more times per day.

In another embodiment, the composition can further include a divalent cation chelator. Suitable divalent cation chelators include ethylenediaminetetraacetate-disodium salt (2-({2-[Bis(carboxymethyl)amino]ethyl}(carboxymethyl)amino)acetic acid); 1,2-Bis(2-amino-5-fluorophenoxy)ethane-N,N,N',N'-tetraacetate-sodium salt; ethylene glycol-bis(β-aminoethyl ether)-N,N,N',N'-tetraacetate-sodium salt; and combinations thereof. Suitable final concentrations of the divalent cation chelator in the composition can range from about 10 µM to about 1 mM.

In another aspect, the present disclosure is directed to a composition including tetraethylammonium chloride (N,N,N,N-Tetraethylammonium chloride) and a lubricant. The amount of tetraethylammonium chloride in the composition varies depending on the desired dose for efficient drug delivery, the molecular weight, and the activity of the compound. The actual amount of the tetraethylammonium chloride can depend on the patient's age, weight, sex, medical condition, disease or any other medical criteria. The actual amount of tetraethylammonium chloride can be determined according to intended use by techniques known in the art. The composition can be administered one or more times per day. The amount of tetraethylammonium chloride thereof included in the composition of the present disclosure can vary, depending upon a variety of factors, including, for example, the desired dosage level, the type and amount of lubricant used, and the presence, types and amounts of additional materials included in the composition. Suitably, the tetraethylammonium chloride ranges from about 1 mM to about 20 mM.

In another aspect, the present disclosure is directed to a composition including potassium and a lubricant. The amount of potassium in the composition varies depending on the desired dose for efficient drug delivery, the molecular weight, and the activity of the compound. The actual amount of the potassium can depend on the patient's age, weight, sex, medical condition, disease or any other medical criteria. The actual amount of potassium can be determined according to intended use by techniques known in the art. The composition can be administered one or more times per day. The amount of potassium thereof included in the composition of the present disclosure can vary, depending upon a variety of factors, including, for example, the desired dosage level, the type and amount of lubricant used, and the presence, types and amounts of additional materials included in the composition. Suitably, potassium can be included in the composition in ranges of from about 10 mM to about 50 mM.

In another aspect, the present disclosure is directed to a composition including a sodium channel activator and a lubricant. Suitable sodium channel activators include, for example, veratridine (4α,9-Epoxy-3β-veratroyloxy-5β-cevan-4β,12,14,16β,17,20-hexaol).

The amount of sodium channel activator in the composition varies depending on the desired dose for efficient drug delivery, the molecular weight, and the activity of the compound. The actual amount of the sodium channel activator can depend on the patient's age, weight, sex, medical condition, disease or any other medical criteria. The actual amount of sodium channel activator can be determined according to intended use by techniques known in the art. The composition can be administered one or more times per day. The amount of sodium channel activator thereof included in the composition of the present disclosure can vary, depending upon a variety of factors, including, for example, the desired dosage level, the type and amount of lubricant used, and the presence, types and amounts of additional materials included in the composition.

Suitably, composition includes the sodium channel activator in an amount ranging from about 10 µM to about 1 mM.

In another aspect, the present disclosure is directed to a composition including a divalent cation chelator and a lubricant. Suitable divalent cation chelators include, for example, ethylenediaminetetraacetate-disodium salt (EDTA) (2-({2-[Bis(carboxymethyl)amino]ethyl}(carboxymethyl)amino)acetic acid); 1,2-Bis(2-amino-5-fluorophenoxy)ethane-N,N,N',N'-tetraacetate-sodium salt (BAPTA); ethylene glycol-bis(β-aminoethyl ether)-N,N,N',N'-tetraacetate-sodium salt (EGTA); and combinations thereof. The divalent cation chelator can lower the concentration of extracellular divalent cations to increase the firing rate of sensory neurons. As known to those skilled in the art, divalent cation chelators stabilize neuronal membranes. Upon reduction of divalent cation concentrations, neurons become more excitable and can fire repetitively (Wang et al., J. Neurosurg. Anesthesiol. 2004; 16:201-209; Sheroziya et al., J. Neurosci. 2009; 29:12131-12144). Further, EDTA has been approved by the U.S. Food and Drug Administration to treat patients with lead intoxication.

The amount of divalent cation chelator in the composition varies depending on the desired dose for efficient drug delivery, the molecular weight, and the activity of the compound. The actual amount of the divalent cation chelator can depend on the patient's age, weight, sex, medical condition, disease or any other medical criteria. The actual amount of divalent cation chelator can be determined according to intended use by techniques known in the art. The composition can be administered one or more times per day. The amount of divalent cation chelator thereof included in the composition of the present disclosure can vary, depending upon a variety of factors, including, for example, the desired dosage level, the type and amount of lubricant used, and the presence, types and amounts of additional materials included in the composition.

The compositions of the present disclosure can also include one or more additional active ingredients, excipients, dissolution agents, surfactants, antioxidants, antiseptics, preservatives, penetrants, and combinations thereof.

Various excipients can be mixed with the compositions as would be known to those skilled in the art. Suitable excipients include, for example, microcrystalline cellulose, colloidal silicon dioxide, lactose, starch, sorbitol, cyclodextrin and combinations thereof.

Suitable dissolution agents include, for example, organic acids such as citric acid, fumaric acid, tartaric acid, succinic acid, ascorbic acid, acetic acid, malic acid, glutaric acid and adipic acid, and can be used alone or in combination. These agents can also be combined with salts of the acids, e.g. sodium citrate with citric acid, to produce a buffer system.

Suitable surfactants include, for example, sodium lauryl sulphate, polyethylene separates, polyethylene sorbitan fatty acid esters, polyoxyethylene castor oil derivatives, polyoxyethylene alkyl ethers, benzyl benzoate, cetrimide, cetyl alcohol, docusate sodium, glyceryl monooleate, glyceryl monostearate, glyceryl palmitostearate, lecithin, medium chain triglycerides, monoethanolamine, oleic acid, poloxamers, polyvinyl alcohol and sorbitan fatty acid esters.

Suitable antioxidants include, for example, sodium metabisulfite; tocopherols such as α, β, δ-tocopherol esters and α-tocopherol acetate; ascorbic acid and pharmaceutically acceptable salts thereof; ascorbyl palmitate; alkyl gallates (e.g., propyl gallate, TENOX® PG, TENOX® S-1); sulfites and pharmaceutically acceptable salts thereof; butylated hydroxyanisole; butylated hydroxytoluene; and monothioglycerol.

Suitable antiseptics include, for example, chlorhexidine gluconate, glucono delta-lactone, methylparaben, sodium hydroxide, and combinations thereof.

Suitable preservatives include parabens. Suitable parabens include, for example, methylparaben (E number E218), ethylparaben (E214), propylparaben (E216), butylparaben and heptylparaben (E209). Less common parabens include isobutylparaben, isopropylparaben, benzylparaben and their sodium salts.

Suitable penetrants include, for example, sulphoxides (e.g., dimethyl sulphoxide, dimethylacetamide, dimethylformamide), azone (1-dodecylazacycloheptan-2-one or laurocapran), pyrrolidones (e.g., N-methyl-2-pyrolidone), fatty acids (e.g., oleic acid, lauric acid, myristic acid, capric acid), essential oils (e.g., eucalyptus, chenopodium, ylang-ylang, L-menthol), terpenes (e.g., sesquiterpene), terpenoids, oxazolidinones (e.g., 4-decyloxazolidin-2-one), and urea.

Methods for Treating Sexual Dysfunction

In another aspect, the present disclosure is directed to a method for treating sexual dysfunction in a subject in need thereof. The method includes topically applying to the subject's genitalia a composition selected from the group consisting of a composition comprising a potassium channel blocker and a lubricant; a composition comprising tetraethylammonium chloride and a lubricant; a composition comprising potassium and a lubricant; a composition comprising a sodium channel activator and a lubricant, and a composition comprising a divalent cation chelator and a lubricant, as described herein.

Suitable subjects include female subjects and male subjects. Further, the subjects are referred to herein as "subjects in need thereof". As used herein, "subjects in need thereof" refers to a subset of subjects in need of increasing sexual arousal. In one embodiment, subjects that are in specific need may include subjects who are susceptible to, or at elevated risk of, diagnosed as suffering from low sex drive, sexual dysfunction, and the like, as well as menopausal and post-menopausal women. Subjects may be susceptible to, or at elevated risk of, diagnosed due to family history, age, environment, and/or lifestyle.

The compositions of the present disclosure can be topically applied in the region of the clitoris and vagina of the female subject. The compositions of the present disclosure can be topically applied to the penis of the male subject. Suitably, the compositions of the present disclosure can be topically applied to the skin and the mucosa of the female genitalia and male genitalia. Typical volumes of compositions to be applied can range from about 0.25 ml to about 5 ml.

The compositions of the instant application can be packaged in amounts for single-use dosages or in larger, multiple dosage packaging.

Methods for Stimulating Erogenous Zones

In another aspect, the present disclosure is directed to a method for stimulating erogenous zones of a subject in need thereof. The method includes topically applying to the subject's genitalia a composition selected from the group consisting of a composition comprising a potassium channel blocker and a lubricant; a composition comprising tetraethylammonium chloride and a lubricant; a composition comprising potassium and a lubricant; a composition comprising a sodium channel activator and a lubricant; and a composition comprising a divalent cation chelator and a lubricant, as described herein.

Suitable subjects include female subjects and male subjects. Further, the subjects are referred to herein as "subjects in need thereof". As used herein, "subjects in need thereof" refers to a subset of subjects in need of stimulating erogenous zones. In one embodiment, subjects that are in specific need may include subjects who are susceptible to, or at elevated risk of, diagnosed as suffering from low sex drive, sexual dysfunction, and the like, as well as menopausal and post-menopausal women. Subjects may be susceptible to, or at elevated risk of, diagnosed due to family history, age, environment, and/or lifestyle.

The compositions of the present disclosure can be topically applied in the region of the clitoris and vagina of the female subject. The compositions of the present disclosure can be topically applied to the penis of the male subject. Suitably, the compositions of the present disclosure can be topically applied to the skin and the mucosa of the female genitalia and male genitalia. Typical volumes of compositions to be applied can range from about 0.25 ml to about 5 ml.

Methods for Treating Female Orgasmic Disorder

In one aspect, the present disclosure is directed to a method for treating female orgasmic disorder in a subject in need thereof. The method includes topically applying to the subject's genitalia a composition selected from the group consisting of a composition comprising a potassium channel blocker and a lubricant; a composition comprising tetraethylammonium chloride and a lubricant; a composition comprising potassium and a lubricant; a composition comprising a sodium channel activator and a lubricant; and a composition comprising a divalent cation chelator and a lubricant, as described herein.

Suitable subjects include female subjects and male subjects. Further, the subjects are referred to herein as "subjects in need thereof". As used herein, "subjects in need thereof" refers to a subset of subjects in need of treatment for female orgasmic disorder. In one embodiment, subjects that are in specific need may include subjects who are susceptible to, or at elevated risk of, diagnosed as suffering from low sex drive, sexual dysfunction, and the like, as well as menopausal and post-menopausal women. Subjects may be susceptible to, or at elevated risk of, diagnosed due to family history, age, environment, and/or lifestyle.

The compositions of the present disclosure can be topically applied in the region of the clitoris and vagina of the female subject. Suitably, the compositions of the present disclosure can be topically applied to the skin and the mucosa of the female genitalia. Typical volumes of compositions to be applied can range from about 0.25 ml to about 5 ml.

The compositions of the instant application can be packaged in amounts for single-use dosages or in larger, multiple dosage packaging.

EXAMPLES

Example 1

In this Example, 4-aminopyridine will be applied to genital mucosa to study the effect on sexual activity.

4-aminopyridine (4-AP) (greater than 99% purity) will be obtained from a commercial supplier (e.g., Sigma-Aldrich, St. Louis, Mo.; Tocris Bioscience, Bristol, UK). 4-AP will be dissolved in sterile physiological saline solution to make a stock concentration of 20 mM. An aliquot of the 4-AP solution will be diluted 10-fold into glycerin and hydroxyethyl cellulose (K-Y JELLY) to achieve a final concentration of 2 mM. Final 4-AP concentrations ranging from about 1 µM to about 10 mM will also be tested. An aliquot (0.25 ml to 10 ml) will be topically applied to the genital mucosa immediately prior to sexual activity.

Subjects will be monitored for sensation experiences such as burning and tingling, among other sensations, in the genital region. Although considered remote because of the low dosage, subjects will also be monitored for seizure.

Example 2

In this Example, a composition including 4-aminopyridine and a divalent cation chelator will be applied to genital mucosa to study the effect on sexual activity.

4-aminopyridine (4-AP) will be obtained from a commercial supplier (e.g., Sigma-Aldrich, St. Louis, Mo.; Tocris Bioscience, Bristol, UK). 4-AP will be dissolved in a sterile physiological saline solution to make a stock concentration of 20 mM. Ethylenediaminetetraacetate-disodium salt (2-({2-[Bis(carboxymethyl)amino]ethyl}(carboxymethyl) amino)acetic acid) (EDTA) will be obtained from a commercial supplier (e.g., Sigma-Aldrich). EDTA will be dissolved in a sterile physiological saline solution to make a stock concentration of mM. The 4-AP solution and the EDTA solution will be diluted into glycerin and hydroxyethyl cellulose (K-Y JELLY) to achieve final 4-AP concentrations ranging from about 1 µM to about 10 mM and final EDTA concentrations ranging from about 10 µM to about 1 mM. An aliquot (0.25 ml to 10 ml) will be topically applied to the genital mucosa immediately prior to sexual activity.

Subjects will be monitored for sensation experiences such as burning and tingling, among other sensations, in the genital region. Although considered remote because of the low dosage, subjects will also be monitored for seizure.

Described herein are compositions and local applications of these compositions that can stimulate erogenous zones of a subject utilizing safe, FDA-approved pharmaceuticals (e.g., 4-AP and EDTA) that have not been previously utilized for the purpose described herein. The common mechanisms of action of these are a blockade of sensory nerve potassium channels or facilitation (activation) of sodium channel opening, both of which will increase the firing of sensory nerve endings in the genital region. Without being bound by theory, it is believed that the compositions of the present disclosure can safely be applied to vaginal and clitoral mucous membranes and rapidly gain access to cutaneous sensory afferent nerve endings. The compositions will enhance the sensitivity of these nerve endings, as demonstrated by references showing an increase the rate of firing of peripheral nerves. This increased neuronal sensitivity should increase the probability of reaching orgasm. The effect will be especially prominent in menopausal and post-menopausal women who have thin vaginal mucosa with fewer cutaneous sensory afferents. While more specifically directed at enhancing female sexual responsiveness, the strategies described in the present disclosure can also be applied to enhance male sexual responsiveness.

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods and materials are described.

What is claimed is:

1. A method for treating sexual dysfunction in a subject in need thereof or for stimulating erogenous zones of a subject in need thereof, the method comprising: topically applying to the subject's genitalia a composition consisting essentially of: a potassium channel blocker selected from the group consisting of 4-aminopyridine; 3,4-diaminopyridine, quinidine ((S)-(6-Methoxyquinolin-4-yl)[(1S,2R,4S,5R)-5-vinylquinuclidin-2-yl]methanol), ibutilide (N-(4-{4-[ethyl (heptyl)amino]-1-hydroxybutyl}phenyl)methanesulfonamide), propafenone (1-{2-[2-Hydroxy-3-(propylamino) propoxy]phenyl}-3-phenylpropan-1-one), amiodarone ((2-{4-[(2-butyl-1-benzofuran-3-yl)carbonyl]-2,6-diiodophenoxy}ethyl)diethylamine), vernakalant ((3R)-1-{(1R,2R)-2-[2-(3,4-dimethoxyphenyl) ethoxy] cyclohexyl}pyrrolidin-3-ol), dofetilide (N-[4-(2-{[2-(4-methane sulfonamidophenoxy)ethyl](methyl)amino}ethyl) phenyl]methanesulfonamide), dronedarone (N-(2-Butyl-3-(p-(3-(dibutylamino)propoxy)benzoyl)-5-benzofuranyl) methanesulfonamide), and combinations thereof and a lubricant selected from the group consisting of glycerin, hydroxyethyl cellulose, xylitol, carrageenan, and combinations thereof; wherein the composition is a topical composition.

2. The method of claim 1, wherein the potassium channel blocker is at least one of 4-aminopyridine and 3,4-diaminopyridine in an amount ranging from about 1 µM to about 10 mM.

3. The method of claim 1, wherein the potassium channel blocker is quinidine, and is present in the composition in an amount ranging from about 10 µM to about 10 mM.

* * * * *